US011298366B2

(12) United States Patent
Karpeisky et al.

(10) Patent No.: US 11,298,366 B2
(45) Date of Patent: Apr. 12, 2022

(54) IBANDRONATE CONJUGATES OF NUCLEOSIDE ANTIMETABOLITES

(71) Applicant: MBC Pharma, Inc., Aurora, CO (US)

(72) Inventors: Alexander Karpeisky, Aurora, CO (US); Shawn Zinnen, Aurora, CO (US)

(73) Assignee: MBC Pharma, Inc, Aurora, CO (US)

( * ) Notice: Subject to any disclaimer, the term of this patent is extended or adjusted under 35 U.S.C. 154(b) by 0 days.

(21) Appl. No.: 16/625,990

(22) PCT Filed: Jan. 5, 2018

(86) PCT No.: PCT/US2018/012687
§ 371 (c)(1),
(2) Date: Dec. 23, 2019

(87) PCT Pub. No.: WO2019/005207
PCT Pub. Date: Jan. 3, 2019

(65) Prior Publication Data
US 2020/0163978 A1 May 28, 2020

Related U.S. Application Data

(60) Provisional application No. 62/524,997, filed on Jun. 26, 2017.

(51) Int. Cl.
| | | |
|---|---|---|
| *A61K 31/663* | (2006.01) | |
| *A61P 35/00* | (2006.01) | |
| *A61K 31/7052* | (2006.01) | |
| *A61K 31/7084* | (2006.01) | |
| *A61K 45/06* | (2006.01) | |

(52) U.S. Cl.
CPC ........ *A61K 31/663* (2013.01); *A61K 31/7052* (2013.01); *A61K 31/7084* (2013.01); *A61P 35/00* (2018.01); *A61K 45/06* (2013.01)

(58) Field of Classification Search
CPC ........ A61K 31/7042–7084; A61K 47/548–55; A61K 51/0489; C07H 19/10; C07H 19/20
See application file for complete search history.

(56) References Cited

U.S. PATENT DOCUMENTS

| | | | |
|---|---|---|---|
| 5,208,066 A | 5/1993 | Fujisaki et al. | |
| 6,214,812 B1 | 4/2001 | Karpeisky et al. | |
| 6,896,871 B2 | 5/2005 | Padioukova et al. | |
| 7,598,246 B2 | 10/2009 | Dixon et al. | |
| 8,586,781 B2 | 11/2013 | Karpeisky et al. | |
| 9,216,204 B2 | 12/2015 | Karpeisky et al. | |
| 2001/0041689 A1 | 11/2001 | Padioukova | |
| 2009/0227544 A1* | 9/2009 | Karpeisky ............ | A61K 47/54 514/102 |

FOREIGN PATENT DOCUMENTS

WO 2018129399 7/2018

OTHER PUBLICATIONS

Ringe, J. et al "A review of bone pain relief with ibandronate . . . " Clin. Exp. Rheumatol., vol. 25, pp. 766-774. (Year: 2007).*
Janjan, N. "Bone metastases: approaches to management" Semin. Oncol, vol. 28 (suppl 11, pp. 28-34. (Year: 2001).*
Chmielewska, E. et al "Physiologic activity of bisphosphonates . . . " Open Pharm. Sci. J., vol. 3, pp. 56-78. (Year: 2016).*
Leu, C. et al "Relative binding affinities of bisphosphonates . . . " Bone, vol. 38, pp. 628-636. (Year: 2006).*
Cole, L. et al "Targeted delivery to bone and mineral deposits . . . "Adv. Drug Deliv. Rev., vol. 99, pp. 12-27. (Year: 2016).*
Baron et al. (2011) "Denosumab and bisphosphonates: Different mechanisms of action and effects" Bone 48(4):677-692.
Barrett-Lee et al. (2014) "Oral Ibandronic Acid Verus Intavenous Zoledronic Acid in Treatment of Bone Metastases from Breast Cancer" a Randomized, Open-Label, Non-Inferiority Phase 3 Trial Lancet Oncol 15(1):114-122.
Bogachev (1995) "Study of the reaction of trifluoroacetic anhydride with thymidine-5'-phosphate" Bioorganicheskaya Khimia (Russ) 21(3):212-217.
Bogachev (1996) "Synthesis of deoxynucleoside 5'-triphosphate using trifluoroacetic anhydride as an activating reagent" Bioorganicheskaya Khimia (Russ) 22(9):699-705.
Caraglia et al. (2006) "Emerging anti-cancer molecular mechanisms of aminobisphosphonates" Endocr Relat Cancer 13(1):7-26.
Cole et al. (2016) "Targeted delivery to bone and mineral deposits using bisphosphonate ligands" Advanced Drug Delivery Reviews 99:12-27.
Graaf et al. (2004) "Effects of statins and farnesyltransferase inhibitors on the development and progression of cancer" Cancer Treatment Reviews 30(7):609-641.
Ibrahim et al. (2003) "Approval summary for zoledronic acid for treatment of multiple myeloma and cancer bone metastases" Clin Cancer Res. 9(7):2394-9.
Kucukzeybek et al. (2010) "Apoptosis-mediated cytotoxic effects of ibandronic acid on hormone- and drug-refractory prostate cancer cells and human breast cancer cells" J Int Med Res 38(5):1663-1672.
Luckman et al. (1998) "Nitrogen-containing bisphosphonates inhibit the mevalonate pathway and prevent post-translational prenylation of GTP-binding proteins, including Ras" J Bone Miner Res 13(4):581-589.
Nilsson et al. (2011) "Mevalonate pathway inhibitors affect anti-cancer drug-induced cell death and DNA damage response of human sarcoma cells" Cancer Lett 304(1):60-69.
Patrick (2012)"Synthesis and Characterization of Macrocyclic Bisphosphonate Dimers" QScience Connect 2012(1).
Rogers et al. (2011) "Biochemical and molecular mechanisms of action of bisphosphonates" Bone 49(1):34-41.
(Continued)

*Primary Examiner* — Leigh C Maier
(74) *Attorney, Agent, or Firm* — FisherBroyles, LLP; Cara L. Crowley-Weber (57) ABSTRACT

Provided herein are conjugates of nucleoside antimetabolites and their analogs with ibandronate, pharmaceutical compositions including one or more of said conjugates, methods of synthesizing the same as well as methods of treating diseases and or conditions using the same.

18 Claims, 3 Drawing Sheets

(56) References Cited

OTHER PUBLICATIONS

Vanek (2008) "Synthesis of Prolinol-Based Phosphonate Nucleotide Analogues" This is a PhD dissertation.
Walker and Olson (2005) "Targeting Ras and Rho GTPases as opportunities for cancer therapeutics" Current Opinion in Genetics & Development 15(1):62-68.
International Preliminary Report on Patentability from PCT/US2018/012687 dated Dec. 31, 2019.
Zinnen (2015) "Novel Bone-Targeting Combination Therapy for Osteosarcoma" https://grantome.com/grant/NIH/R43-CA203166-01.
El-Mabhouh et al. (2011) "A conjugate of gemcitabine with bisphosphonate (Gem/BP) Shows Potential as a targeted bone-specific therapeutic agent in an animal model of human breast cancer bone metastases" Oncology Research 19:287-295.

\* cited by examiner

IBANDRONATE CONJUGATES OF NUCLEOSIDE ANTIMETABOLITES

CROSS-REFERENCE TO RELATED APPLICATIONS

This application is a National Stage Application of PCT/US2018/012687, filed Jan. 5, 2018, which claims the benefit under 35 USC § 119(e) of U.S. Provisional Application No. 62/524,997, filed Jun. 26, 2017, each of which are incorporated herein by reference. To the extent appropriate, a claim of priority is made to each of the above-disclosed applications.

TECHNICAL FIELD

Provided herein are compounds and methods of using them related to the field of chemistry, biochemistry and medicine. More particularly, disclosed herein are conjugates of nucleoside antimetabolites and their analogs with ibandronate, pharmaceutical compositions including one or more of said conjugates, methods of synthesizing the same as well as methods of treating diseases and or conditions using the same.

BACKGROUND

Delivery of active compounds to a patient in need is typically achieved by systemic administration, for example, via intravenous or oral routes. Such systemic delivery exposes healthy cells and tissues to the drug even though the drug is needed only in a certain area of the body. As a result, healthy cells and tissues can be adversely affected by the drug, and significantly higher concentrations of the drug are necessary to deliver pharmacologically relevant levels to the site needing treatment.

Compositions and methods provided herein address this and other problems in the art.

SUMMARY

Provided herein are compounds, compositions comprising those compounds, methods of making those compounds, and methods of using those compounds.

One aspect relates to compounds of Formula I or pharmaceutically acceptable salts thereof.

Another aspect relates to compounds of Formula II or pharmaceutically acceptable salts thereof.

Further disclosed herein are methods of synthesis of the compounds of Formulae I and II.

Still further disclosed herein are methods of delivering nucleoside antimetabolites and their analogs to the bone by conjugating said compounds with ibandronate.

Also disclosed herein are pharmaceutical compositions comprising one or more compounds of Formula I and/or II, one or more pharmaceutically acceptable carriers, diluent excipients or combinations thereof.

Some aspects of the methods disclosed herein relate to treating diseases and/or ameliorating the symptoms of diseases, including but not limited to cancer, cancer-induced bone disease, primary bone cancer, bone metastases and pain, by administering to a patient in need thereof a therapeutically effective amount of one or more compounds of Formulae I and/or II or a pharmaceutical composition including the said compounds. Such compounds can be used in manufacture of medicaments used for the treatment of said diseases. Such compounds can be used in treating a variety of diseases.

BRIEF DESCRIPTION OF THE FIGURES

Mice were treated with saline, or equimolar doses of ibandronate (Iband), gemcitabine (Gem), gemcitabine-etidronate conjugate (Gem-Eti), or with the gemcitabine-ibandronate conjugate 5 (Gem-Ibad).

DETAILED DESCRIPTION

Nucleoside antimetabolites represent a class of nucleoside analogs with broad therapeutic use and biologic activity, for example antitumor activity and/or antiviral activity. These compounds mimic physiological nucleosides in terms of uptake and metabolism and are incorporated into newly synthesized DNA resulting in inhibition of DNA synthesis and termination of the growing chain. Some of these drugs also affect nucleotide generation, RNA synthesis, and activate the caspase cascade. All of these activities lead to cell death. Nucleoside analogs as such are therapeutically inactive and are converted by host or viral enzymes to their active forms, and subsequently inhibit nucleotide-polymerizing enzymes and other nucleotide-dependent enzymes involved in cell or viral metabolism and survival. This activation occurs by metabolic transformation of nucleoside analogs to their respective 5'-mono-, di- and triphosphates.

Ibandronate is a third-generation nitrogen-containing bisphosphonate used in treatment of osteoporosis; mechanistically the compound affects osteoclasts by inhibiting isoprenylation of the small GTP-binding proteins. In addition to its effects on bone, there is growing evidence for ibandronate's anticancer activity 1-8. However, the mechanisms involved in these effects remain poorly understood.

The use of bisphosphonates to deliver other drugs to the bone due to their high affinity to the bone mineral have been proposed before (see e.g. U.S. Pat. No. 6,214,812 to Karpeisky, M. et al.; U.S. Pat. No. 8,586,781 to Karpeisky, A. et al.; U.S. Pat. No. 9,216,204 to Karpeisky, A et al.; and recent review[9]). One such compound, MBC-11, a conjugate of cytarabine with etidronate (see e.g., U.S. Pat. No. 7,598,246 to Dixon et al.; U.S. Pat. No. 6,896,871 to Karpeisky et al.), is currently in clinical development. Disclosed herein are conjugates of ibandronate determined to have improved survival in an animal models of breast cancer or prostate cancer induced bone disease: see FIG. 1 and FIG. 2 respectively. Also observed was a decrease in secondary non-osseous metastases. These conjugates would not have been predicted to have such activity, suggesting a novel and unique improvement and benefit when ibandronate is the bone targeting moiety.

Disclosed herein are novel ibandronate derivatives of nucleoside antimetabolites and their analogs, for use in the treatment of, for example, neoplastic and bone diseases.

Unless defined otherwise, all technical and scientific terms used throughout this application have the meanings that are commonly understood by one of ordinary skill in the art.

As used herein, an "alkyl" group refers to a saturated aliphatic hydrocarbon, including straight-chain or branched-chain alkyl groups. In some embodiments, the alkyl group has 1 to 20 carbons. In some aspects, the alkyl group is a lower alkyl having from 1 to 10 carbons, or from 1 to 6 carbons. The alkyl group may be substituted or unsubstituted. When substituted, the substituent group(s) may include hydroxy, cyano, alkoxy, $NO_2$ or $N(CH_3)_2$, amino, $N_3$ or SH.

As used herein, a "cycloalkyl" group refers to a cyclic alkyl group having from three to ten, or, for example, five or six carbon atoms forming the alkyl ring.

As used herein, an "aryl" group refers to an aromatic group which has at least one ring having a conjugated pi electron system and includes carbocyclic aryl, heterocyclic aryl and biaryl groups, any of which may be optionally substituted. Substituent(s) on these groups may include halogen, trihalomethyl, hydroxyl, SH, cyano, alkoxy, alkyl, alkenyl, alkynyl, and amino groups.

As used herein, "heteroaryl" refers to an aromatic ring having from 1 to 3 heteroatoms in the aromatic ring with the remainder of the atoms in the ring being carbon atoms. Suitable heteroatoms include oxygen, sulfur, and nitrogen, and exemplary heteroaryls include furanyl, thienyl, pyridyl, pyrrolyl, pyrrolo, pyrimidyl, pyrazinyl and imidazolyl. These heteroaryl rings may also be substituted. Substituents on these heteroaryl groups may include halogen, trihalomethyl, hydroxyl, SH, cyano, alkoxy, alkyl, alkenyl, alkynyl, and amino groups.

As used herein, "anti-cancer compound" or "compound having anticancer activity" refers to any compound demonstrating preclinical or clinical anti-cancer activity or used in clinics for treating patients suffering with cancer.

As used herein, an "unmodified nucleic (or heterocyclic) base" or "natural nucleic base" is any base found in a nucleic acid including adenine, cytosine, guanine, uracil, and thymine having no additional substituents or modifications.

As used herein, a "modified nucleic (or heterocyclic) base" is any base found in a nucleic acid which contains any modification in the chemical structure relative to an unmodified nucleic base.

As used herein, an "unmodified sugar" is beta-D-ribofuranose or 2-deoxy-beta-D-ribofuranose.

As used herein, a "modified sugar" is any sugar moiety containing any modification in the chemical structure of an unmodified sugar.

A nucleoside antimetabolite X is attached to the chemical structures provided herein as a residue or moiety, via substitution of the hydrogen atom in 5'-OH, 2'-OH or 3'-OH position in its molecule.

It is understood that, in any compound described herein having one or more chiral centers, if an absolute stereochemistry is not expressly indicated, then each center may independently be of R-configuration or S-configuration or a mixture thereof. Hence, the compounds provided herein may be enantiomerically pure or be stereoisomeric mixtures. It is also understood that, in any compound described herein having one or more double bond(s) generating geometrical isomers that can be defined as E or Z, each double bond may independently be E or Z or a mixture thereof. Likewise, all tautomeric forms are also intended to be included.

In some embodiments, compounds disclosed herein have the chemical structure I wherein X is an anticancer compound and Y is selected from H, alkyl, aryl, substituted aryl, heteroaryl, substituted heteroaryl. The anticancer compound is selected from the compounds which demonstrated anticancer activity on the cell, animal, or human level.

In other embodiments disclosed herein are the compounds of formula I, wherein X is nucleoside antimetabolite or nucleoside analog. Examples of nucleoside antimetabolites or nucleoside analogs include but are not limited to cytarabine, gemcitabine, clofarabine, cladribine, vidaza, dacogen, fludarabine, floxuridine, nelarabine and pentostatin.

Yet in other embodiments disclosed herein are the compounds of formula I, wherein X is selected from the group comprising nucleoside antimetabolites and having structure:

where B is natural or modified nucleic acid base,
R4=H,
R2 and R3 are independently selected from the group consisting of H, OH, F, Cl Another embodiment relates to the compounds having chemical structure II:

wherein X is anticancer compound and Y is selected from H, alkyl, aryl, substituted aryl, heteroaryl, and substituted heteroaryl. The anticancer compound is selected from the compounds which demonstrated anticancer activity on the cell, animal, or human level.

In other embodiments disclosed herein are the compounds of formula II, wherein X is nucleoside antimetabolite or nucleoside analog. Examples of nucleoside antimetabolites or nucleoside analogs include but are not limited to cytarabine, gemcitabine, clofarabine, cladribine, vidaza, dacogen, fludarabine, floxuridine, nelarabine and pentostatin.

In another embodiment disclosed herein are the compounds of formula II, wherein X comprises where B is natural or modified nucleic acid base,
$R^2$ and $R^3$ are independently selected from the group consisting of H, OH, F, Cl.

TABLE 1

Exemplary anticancer nucleoside antimetabolites

Vidaza

Dacogen

Gemcitabine

TABLE 1-continued

Exemplary anticancer nucleoside antimetabolites

Cytarabine

Floxuridine

Pentostatin

Cladribine

Clofarabine

TABLE 1-continued

Exemplary anticancer nucleoside antimetabolites

Fludarabine

Nelarabine

The exemplary nucleosides shown in Table 1 can attach as X in their 5'-, 2', or 3'-nucleosidyl—residue or analog forms, e.g. can attach through the 5'-O—, 2'-O— or 3'-O.

Also contemplated herein are the pharmaceutically acceptable non-toxic acid addition salts of the compounds described herein and pharmaceutically acceptable formulations containing them. Such salts include those derived from organic and inorganic acids such as, without limitation, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embonic acid, enanthic acid, and the like.

The pharmaceutical compositions described herein are preferably formulated in unit dosage form, meaning physically discrete units suitable as a unitary dosage, or a predetermined fraction of a unitary dose to be administered in a single or multiple dosage regimen to human subjects and other mammals, each unit containing a predetermined quantity of active material calculated to produce the desired therapeutic effect in association with a suitable pharmaceutical excipient or excipients. The compositions can be formulated so as to provide sustained or delayed release of active ingredient after administration to the patient by employing procedures well known in the art.

Pharmaceutical compositions provided herein comprise one or more compounds of formulae I and/or II associated with at least one pharmaceutically acceptable carrier, diluent or excipient. In preparing such compositions, the active ingredients are usually mixed with or diluted by an excipient or enclosed within such a carrier, which can be in the form of a capsule or sachet. When the excipient serves as a diluent, it may be a solid, semi-solid, or liquid material, which acts as a vehicle, carrier, or medium for the active ingredient. Thus, the compositions can be in the form of tablets, pills, powders, elixirs, suspensions, emulsions, solutions, syrups, soft and hard gelatin capsules, suppositories, sterile injectable solutions and sterile packaged powders.

Examples of suitable excipients include lactose, dextrose, sucrose, sorbitol, mannitol, starch, gum acacia, calcium silicate, calcium phosphate, alginates, tragacanth, gelatin, microcrystalline cellulose, polyvinylpyrrolidinone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

In preparing a pharmaceutical formulation comprising one or more compounds described herein, it may be necessary to mill the active compound to provide the appropriate particle size prior to combining with the other ingredients. If the active compound is substantially insoluble, it is ordinarily milled to a particle size of less than 200 mesh. If the active compound is substantially water soluble, the particle size is normally adjusted by milling to provide a substantially uniform distribution in the formulation, e.g. about 40 mesh.

Another embodiment provided herein relates to the method of delivering anticancer compounds to the bone by conjugating said compounds with ibandronate. In some aspects, the resulting conjugates have the general structures disclosed in formulae I or II.

Another embodiment provided herein is a novel compound of formulae I or II or a pharmaceutical composition comprising a novel compound of formulae I or II for use in ameliorating or treatment of neoplastic diseases, bone diseases, and cancer-induced bone diseases (including, for example, any cancer from any tissue, including primary bone cancers and metastatic cancer).

Another embodiment provided herein is a novel compound of formulae I or II or a pharmaceutical composition comprising a novel compound of formulae I or II for use in ameliorating or treatment of pain.

As used herein, the terms "ameliorating" or "ameliorate" indicate an improvement or bettering of a disease, an infection, a condition, or pain, e.g. to make more tolerable.

As used herein, the terms "treat" or "treatment" refer to both therapeutic treatment and prophylactic, maintenance, or preventative measures, wherein the object is to prevent an undesired physiological condition, or obtain beneficial or desired clinical results including a reduction in the severity of symptoms or diminishing the underlying causes of the symptoms. Exemplary symptoms include bone pain, pathological fractures, spinal compression, and overall diminished quality of life. Treatment includes eliciting a clinically significant response, without excessive levels of side effects. Successful treatment includes decresed observation of skeletal related events such as pathologic fracture, spinal cord compression, necessity for radiation to bone (for pain or impending fracture) or surgery to bone. See Ibrahim A, Scher N, Williams G, et al. Approval summary for zoledronic acid for treatment of multiple myeloma and cancer bone metastases. Clin Cancer Res. 2003; 9:2394-9.

Neoplastic diseases include but are not limited to cancer, leukemia, and metastatic disease.

Other embodiments provided herein are novel compounds of formulae I or II or their pharmaceutical compositions for use in ameliorating or treatment of pain.

In other embodiments, any of the compounds according to formulae I or II or their pharmaceutical compositions can be used as a medicament.

In further embodiments, any of the compounds according to formulae I or II or their pharmaceutical compositions can be used in the therapy of a neoplastic disease, or pain.

In still further embodiments, any of the compounds according to formulae I or II or their pharmaceutical compositions can be used for the manufacture of a medicament for the treatment of a neoplastic disease, or pain.

Another embodiment provided herein is a method of delivering anticancer nucleoside antimetabolites and their analogs to the bone and surrounding tissue using the compounds of formulae I or II or the pharmaceutical compositions comprising such compounds.

One of ordinary skill in the art will recognize that compounds of the invention structurally resemble nucleoside triphosphates. The compounds of the invention differ from conventional nucleoside triphosphates in the bridging atom between beta and gamma phosphorous atoms: 0 (triphosphates) versus C (compounds of the invention). Provided herein is the method of making ibandronate conjugates based on the nucleoside triphosphate synthesis by Bogachee[10,11]. Methods of nucleoside triphosphate synthesis are known in the art (see for example Vaghefi[12]) and can be modified by skilled artisans to be used for preparation of ibandronate conjugates of the invention.

Additional objects, advantages, and novel features of this invention will become apparent to those skilled in the art upon examination of the following examples thereof, which are not intended to be limiting.

Various publications are cited herein, the disclosures of which are incorporated by reference in their entireties. Such publications can provide exemplary, procedural or other details supplementary to those set forth herein. Nothing herein is to be construed as an admission that the present disclosure is not entitled to antedate such publication by virtue of prior invention. Further, the dates of publication provided may be different from the actual publication dates which may need to be independently confirmed.

While embodiments of the invention have been shown and described, modifications thereof can be made by one skilled in the art without departing from the spirit and teachings of the disclosure. The embodiments described herein are exemplary only, and are not intended to be limiting. Many variations and modifications of the compounds and methods disclosed herein are possible and are within the scope of the invention. Where numerical ranges or limitations are expressly stated, such express ranges or limitations should be understood to include iterative ranges or limitations of like magnitude falling within the expressly stated ranges or limitations. Use of broader terms such as comprises, includes, having, etc. should be understood to provide support for narrower terms such as consisting of, consisting essentially of, comprised substantially of, and the like. Accordingly, the scope of protection is not limited by the description set out above but is only limited by the claims which follow, that scope including all equivalents of the subject matter of the claims. Each and every original claim is incorporated into the specification as an embodiment of the invention. Thus, the claims are a further description and are an addition to the preferred embodiments disclosed herein.

EXAMPLES

Example 1. Gemcitabine-Ibandronate Conjugate 5

MW : 662.19
4

MW : 644.39
5

To the mixture of Gemcitabine-5'-phosphate (1, 1.03 g, 3 mmol), dimethylaniline (1.51 ml, 12.01 mmol) and triethylamine (418.31 ul, 3 mmol) in anhydrous MeCN (10 ml) cooled on an ice bath under positive pressure of Ar (balloon) and stirring was added the cold solution of trifluoroacetic anhydride (TFAA, 2.5 ml, 18 mmol) in MeCN (10 ml) dropwise. The suspension became clear solution indicating formation of anhydride 2 (dark yellow solution). Reaction mix stirred at RT for 15 minutes and then connected to vacuum line to remove the excess of TFAA/TFA. After 15 min, mixture of N-methyl imidazole (NMI, 1.2 ml, 15.01 mmol) and Et3N (3.35 ml, 2.24 mmol) in MeCN (10 ml) was added at 0° C. and stirring. After 5 min, the ice bath was removed and the reaction mix was stirred at RT for 20 min (light yellow solution). Then the solution of ibandronate Bu3N salt in MeCN (20 ml, stored over molecular sieves for 1 h) was added via cannula and the reaction was stirred at RT for 10 minutes. Then 50 mM triethylammonium acetate (TEAA) buffer pH 5.4 (60 ml) was added and solution was extracted with DCM (2×60 ml). Combined organic extract was back extracted with buffer (60 ml). Combined water extracts were separated and pH adjusted to 5.3-5.5 with 50% aq AcOH, divided into 4 equal (40 mL) volumes and frozen until purification. One portion was thawed, diluted to 100 mL with 50 mm TEAA pH 5.3-5.5 and loaded onto a column with Sepra C18-E (50 μm, 65 A; 50 mL). The column was eluted with 50 mM TEAA pH 5.3 (800 ml) then 4% MecN in 50 mM TEAA pH 5.3, and finally with 10% MeCN in the same buffer. Appropriate fractions were pooled and 1M LiOAc was added to make the final concentration of LiOAc 60 mM. Solution was concentrated to 15 ml on a rotary evaporator at <30° C. bath temperature and the title compound was precipitated with 200 mL Acetone-MeOH mix (4:1). The mix left at refrigerator for 60 min and residue separated by centrifugation (3000 rpm, 3 min, 4° C.). The precipitate was washed with the same mix 2 times and dried on high vacuum to produce 230 mg of the conjugate as Li-salt. The latter was dissolved in water and passed through Dowex 50Wx8 (H+) and lyophilized to give 200 mg of conjugate 5.

1H NMR (400 MHz, D2O) δ (ppm): 7.9 (d, J=10 Hz, 1H), 6.3 (m, 1H), 6.1 (d, J=9.6 Hz, 1H), 4.7 (m, 1H), 4.4 (m, 2H), 4.2 (m, 1H), 1.54 (t, J=20 Hz, 3H). 31P NMR (D2O) δ (ppm): 17.2 (m, 1P), 15.9-15.3 (m, 1P), −9.0 (d, 1P).

HPLC Conditions:
Column: Kinetex 5 u XB-C18 100A 4.6×100 mm (Phenomenex).
Mobile phase: A—20 mM triethylammonium acetate (TEAA); B—50% acetonitrile/20 mM TEAA
Linear gradient from 0 to 20% B in 15 min
Flow rate: 1 ml/min
Detection—274 nm Example 2. Cytarabine-Ibandronate Conjugate

MW : 323.20
6

To the mixture of cytarabine-5'-phosphate (araCMP, 850 mg, 2.63 mmol) N, N-dimethylaniline (1.28 mL, 10.24 mmol) and Et$_3$N (374 uL, 2.73 mmol) in anhydrous MeCN (10 ml) cooled on an ice bath under positive pressure of Ar (balloon) and stirring was added the cold solution of TFAA (1.02 mL, 13.6 mmol) in MeCN (10 ml) dropwise. The suspension became clear solution indicating formation of anhydride 7 (dark yellow solution). Reaction mixture stirred at RT for 15 minutes and then connected to vacuum line to remove the excess of TFAA/TFA. After 15 min mixture of NMI (629 uL, 14.14 mmol) and Et$_3$N (1.84 mL, 23.8 mmol) in CH$_3$CN (10 mL) was added at 0° C. and stirring. After 5 min, the ice bath was removed and the reaction mix was stirred at room temperature for 20 min (light yellow solution). Then the solution of ibandronate Bu$_3$N salt (7 g) in MeCN (35 ml, stored over molecular sieves for 1 h) was added via cannula and the reaction was stirred at room temperature for 10 minutes.

The reaction was quenched by addition of water (40 mL) and extracted with DCM (2×40 mL) to remove organic bases. The aqueous layer was diluted with triethylammonium bicarbonate buffer (TEAB, 0.1M, pH 6.8) and loaded onto column with Amberchrome CG61M (113 mL). After the loading was complete, the column was eluted with TEAB (5 CV) and then DI water (8 CV). Finally, the conjugate was eluted out with CH$_3$CN—H$_2$O (1:4 to 1:3). Appropriate fractions were combined and concentrated in vacuo with bath temperature <30° C. to a volume less than 50 mL. The obtained concentrate was lyophilized, to provide conjugate as Et$_3$N salt (9). Yield: 512 mg (33%)

Example 3. Sodium Salt of Cytarabine-Ibandronate Conjugate

Portion of the triethylammonium salt of the conjugate obtained above (330 mg, 0.35 mmol) was dissolved in water (10 mL) and passed through Dowex 50WX8 (Na form) (7 mL, 10×). The column was continuously eluted with water and UV active portions were collected and analyzed by HPLC. Pure fractions were collected and lyophilized to provide conjugate as sodium salt (10). Yield: 144 mg, 60%.

1H NMR (400 MHz, D2O) δ (ppm): 8.0 (d, J=10.2 Hz, 1H), 6.2 (d, J=7.2 Hz, 10, 2H), 4.7 (m, 1H), 4.1 (m, 1H), 4.3 (m, 2H), 4.4 (m, 1H), 3.6 (m, 1H), 3.4-3.3 (m, 1H), 3.3-3.2 (m, 1H), 3.0 (m, 1H), 2.8 (s, 3H), 2.5-2.3 (m, 2H), 1.7 (m, 2H), 1.3 (m, 4H), 0.9 (m, 3H). 31P NMR (D2O) δ (ppm): 16.8 (m, 1P), 10.4-9.8 (m, 1P), −8.8 (d, 1P).

Figure 1:
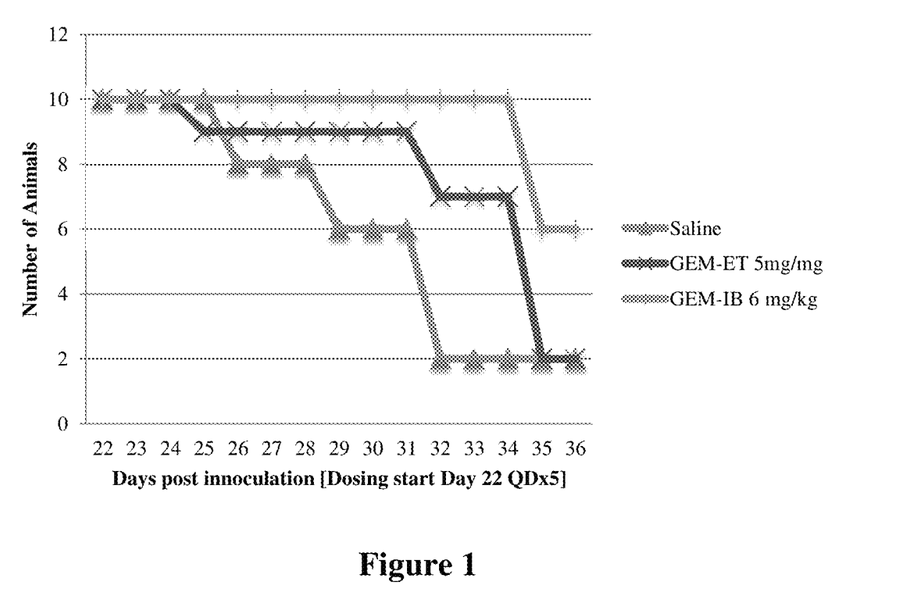
FIG. 1 provides Kaplan-Meier survival curves: a murine model of breast cancer of mice treated with saline gemcitabine-ibandronate conjugate (GEM-IB) or gemcitabine-etidronate conjugate (GEM-ET).

Example 4. Demonstration of Gemcitabine-Ibandronate Conjugate 5 and Gemcitabine-Etidronate Conjugate Providing Survival Benefit in a Rodent Model of Breast Cancer Female Harlan nude mice (Hsd:Athymic Nude-Foxn1nu) of 8 weeks age were administered a 100 uL intracardiac injection of MDA-MB-231-luc-D3H2LN cells (Caliper/Xenogen) at106 cells/mL in Dulbecco's Phosphate Buffered Saline. Twenty-two days after implantation the animals were randomized into groups of 10. Each group received one of the following agents 5 days per week (QDx5) as a 100 uL intraperitoneal injection to achieve a dosing of: saline, 5 mg/kg gemcitabine-ibandronate conjugate, 6 mg/mg gemcitabine-etidronate conjugate, equimolar free etidronate, equimolar free ibandronate, equimolar free gemcitabine. Free etidronate, ibandronate or gemcitabine did not have a significant effect on survival, however, as shown in FIG. 1 both gemcitabine-ibandronate conjugate and gemcitabine-etidronate conjugate improved survival with gemcitabine-ibandronate conjugate providing the greatest benefit.

Figure 2:
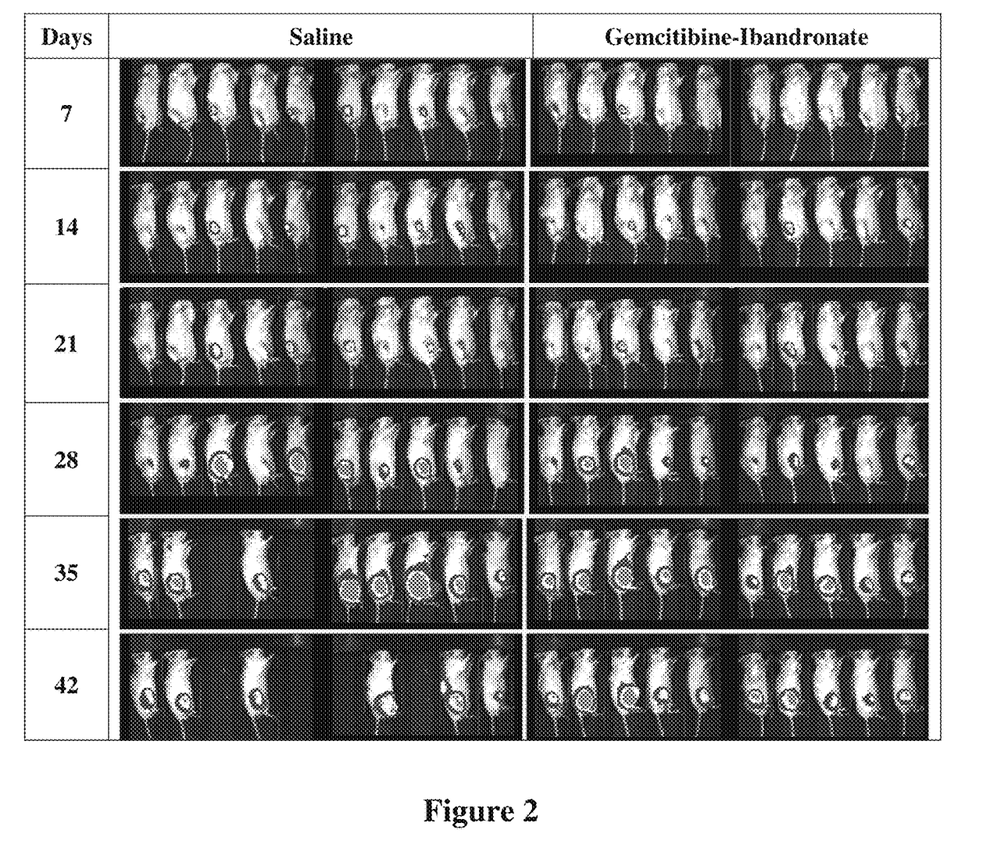
FIG. 2 shows an image analysis of a prostate cancer induced bone disease model untreated (Saline) or treated QDx5 with 2 mg/kg gemcitabine-ibandronate.

Example 5. Demonstration of Gemcitabine-Ibandronate Conjugate 5 Providing Survival Benefit in a Rodent Model of Prostate Cancer Induced Bone Disease Six-week old male SCID mice were injected with 10 uL of $10^6$ 22 RV1-Luc+ prostate cancer cells into the tibia. Luminescence on day 6 confirmed implantation and mice were randomized into groups of 10 and began dosing on day 7. Mice received intraperitoneal injections 5 days/week of saline or 2 mg/kg gemcitibine-ibandronate conjugate (compound 5, example 1) until the end of week 6 and were imaged every 7 days. A Xenogen imaging station was used to visualize tumor cells; the heat map from light blue to red indicates increasing tumor cells numbers. As shown in FIG. 2, all mice treated with the compound 5 (example 1) were alive at the end of 42 days while the untreated saline control had only 6 of 10 mice remaining alive. In addition, the image analysis indicates from day 28 and later, less cancer cells are present in the mice treated with the compound 5.

Example 6. Demonstration of Gemcitabine-Ibandronate Conjugate and Gemcitabine-Etidronate Conjugate Reducing the Incidence of Metastases in a Rodent Model of Prostate Cancer Induced Bone Disease

Figure 3:
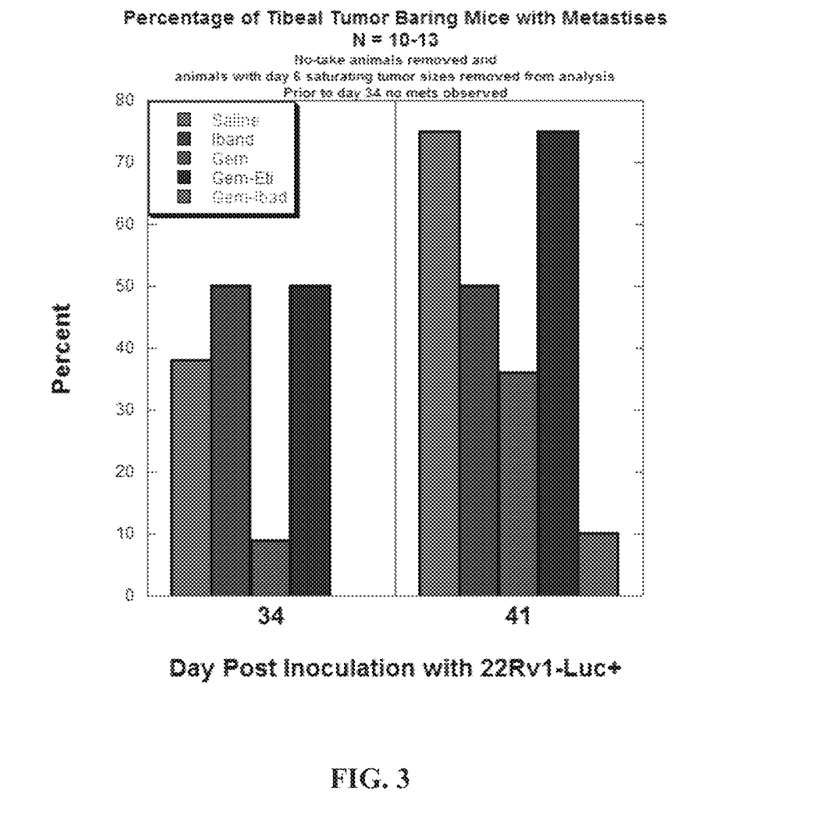
FIG. 3 shows metastases in a mouse model of prostate cancer induced bone disease.

As above in example 5, six-week old male SCID mice were injected with 10 uL of $10^6$ 22 RV1-Luc+ prostate cancer cells into the tibia. Luminescence on day 6 confirmed implantation and mice were randomized into groups of 10-13 and began dosing on day 7. Mice received intraperitoneal injections QDx5 (5 days/week) of saline or 2 mg/kg gemcitibine-ibandronate conjugate or the molar equivalent of gemcitabine-etidronate conjugate, free ibandronate, or free gemcitibine until the end of week 6 and were imaged every 7 days. A Xenogen imaging station was used to visualize tumor cells and metastases distal to the tibial site of implantation. As shown in FIG. 3, both gemcitabine-ibandronate conjugate and gemcitabine-etidronate conjugate reduced the percent of mice with distal metastases at day 34 and day 41. The superior benefit was observed with mice treated with the gemcitabine-ibandronate conjugate.

PUBLICATIONS

1. Baron, R., Ferrari, S., and Russell, R. G. G. (2011) Denosumab and bisphosphonates: Different mechanisms of action and effects, Bone 48, 677-692.
2. Caraglia, M., Santini, D., Marra, M., Vincenzi, B., Tonini, G., and Budillon, A. (2006) Emerging anti-cancer molecular mechanisms of aminobisphosphonates, Endocr Relat Cancer 13, 7-26.
3. Graaf, M. R., Richel, D. J., van Noorden, C. J. F., and Guchelaar, H.-J. (2004) Effects of statins and farnesyltransferase inhibitors on the development and progression of cancer, Cancer Treatment Reviews 30, 609-641.
4. Kucukzeybek, Y., Gorumlu, G., Cengiz, E., Karabulut, B., Sezgin, C., Atmaca, H., Sanli, U. A., Uzunoglu, S., and Uslu, R. (2010) Apoptosis-mediated cytotoxic effects of ibandronic acid on hormone- and drug-refractory prostate cancer cells and human breast cancer cells, J Int Med Res 38, 1663-1672.
5. Luckman, S. P., Hughes, D. E., Coxon, F. P., Graham, R., Russell, G., and Rogers, M. J. (1998) Nitrogen-containing bisphosphonates inhibit the mevalonate pathway and prevent post-translational prenylation of GTP-binding proteins, including Ras, J Bone Miner Res 13, 581-589.
6. Nilsson, S., Huelsenbeck, J., and Fritz, G. (2011) Mevalonate pathway inhibitors affect anticancer drug-induced cell death and DNA damage response of human sarcoma cells, Cancer Lett 304, 60-69.
7. Rogers, M. J., Crockett, J. C., Coxon, F. P., and Monkkonen, J. (2011) Biochemical and molecular mechanisms of action of bisphosphonates, Bone 49, 34-41.
8. Walker, K., and Olson, M. F. (2005) Targeting Ras and Rho GTPases as opportunities for cancer therapeutics, Current Opinion in Genetics & Development 15, 62-68.
9. Cole, L. E., Vargo-Gogola, T., and Roeder, R. K. (2016) Targeted delivery to bone and mineral deposits using bisphosphonate ligands, Advanced drug delivery reviews 99, 12-27.
10. Bogachev, V. S. (1995) Study of the reaction of trifluoroacetic anhydride with thymidine-5'-phosphate, Bioorganicheskaya Khimia (Russ) 21, 212-217.
11. Bogachev, V. S. (1996) Synthesis od deoxynucleoside 5'-triphosphate using trifluoroacetic anhydride as an activating reagent, Bioorganicheskaya Khimia (Russ) 22, 699-705.
12. Monir-Vaghefi, S.-M. (2005) Nucleoside triphosphates and their analogs: chemistry, biotechnology, and biological applications, Taylor & Francis, Boca Raton.

What is claimed is:

1. A compound comprising:

or a pharmaceutically acceptable acid addition salt thereof, wherein;

X is an anticancer compound comprising a nucleoside antimetabolite having the structure:

wherein:

B is a natural or modified nucleic acid base, $R^4$=H, and

$R^2$ and $R^3$ are independently selected from the group consisting of H, OH, F, and Cl; and Y is selected from the group consisting of H, alkyl, aryl, substituted aryl, heteroaryl, and substituted heteroaryl.

2. A compound comprising:

or a pharmaceutically acceptable acid addition salt thereof,
wherein;
X is an anticancer compound comprising a nucleoside antimetabolite having the structure:

wherein:
B is a natural or modified nucleic acid base,
$R^2$ and $R^3$ are independently selected from the group consisting of H, OH, F, and Cl; and
Y is selected from the group consisting of H, alkyl, aryl, substituted aryl, heteroaryl, and substituted heteroaryl.

3. A compound of claim 1, where X is selected from the group consisting of cytarabine, gemcitabine, clofarabine, cladribine, vidaza, dacogen, fludarabine, floxuridine, nelarabine and pentostatin.

4. A pharmaceutical composition comprising a compound of claim 1 and a pharmaceutically acceptable carrier or diluent.

5. A method of treating cancer-induced bone disease or primary bone cancer, or preventing bone metastases, or treating or ameliorating at least one symptom of bone cancer or cancer-induced bone disease, or decreasing the frequency or severity of at least one symptom of bone cancer or cancer-induced bone disease, the method comprising administering a therapeutically effective amount of a compound of claim 1 to a subject in need thereof.

6. A method for delivering of nucleoside antimetabolites to bone or surrounding tissues, the method comprising administering a therapeutically effective amount of a compound of claim 1 to a subject in need thereof.

7. The method of claim 5, wherein the compound is administered in combination with one or more therapeutic agents.

8. The method of claim 5, wherein the compound or the pharmaceutical composition is administered subcutaneously, intravenously, intradermally, intramuscularly, intranasally, or orally.

9. A method of synthesizing nucleoside antimetabolite ibandronate conjugates, the method comprising reacting nucleoside-5'-phosphate or nucleoside-2'- or 3'-phosphate with trifluoroacetic anhydride in the presence of tertiary amine base in organic solvent, followed by addition of nucleophilic catalyst, followed by addition of ibandronate, followed by addition of water and purification by ion-exchange or reverse-phase chromatography.

10. The method of claim 9 where tertiary amine is selected from the group consisting of triethylamine, dimethylaniline, and pyridine.

11. The method of claim 9, where said nucleophilic catalyst is selected from the group consisting of dimethylaminopyridine and N-methylimidazole.

12. The method of claim 9, where organic solvent is selected from the group consisting of acetonitrile, pyridine, dimethylformamide, and dimethylacetamide.

13. The method of claim 5, wherein the symptom of bone cancer or bone disease is pain.

14. The method of claim 5, wherein the primary cancer is prostate cancer or breast cancer.

15. The method of claim 5, wherein the treatment results in increased survival compared to a similarly situated subject without treatment.

16. The method of claim 5, wherein the treatment results in decreased formation of secondary non-osseous metastases compared to a similarly situated subject without treatment.

17. A compound of claim 2, where X is selected from the group consisting of cytarabine, gemcitabine, clofarabine, cladribine, vidaza, dacogen, fludarabine, floxuridine, nelarabine and pentostatin.

18. A pharmaceutical composition comprising a compound of claim 2 and a pharmaceutically acceptable carrier or diluent.

* * * * *

UNITED STATES PATENT AND TRADEMARK OFFICE
CERTIFICATE OF CORRECTION

PATENT NO. : 11,298,366 B2
APPLICATION NO. : 16/625990
DATED : April 12, 2022
INVENTOR(S) : Karpeisky et al.

It is certified that error appears in the above-identified patent and that said Letters Patent is hereby corrected as shown below:

In the Claims

Column 16, Line 32, should read as follows:
1. A compound comprising:

or a pharmaceutically acceptable acid addition salt thereof,
wherein:
X is an anticancer compound comprising a nucleoside antimetabolite having the structure:

wherein:
    B is a natural or modified nucleic acid base,
    $R^4$=H, and
    $R^2$ and $R^3$ are independently selected from the group consisting of H, OH, F, and Cl;
and
    Y is selected from the group consisting of H, alkyl, aryl, substituted aryl, heteroaryl, and substituted heteroaryl.

Signed and Sealed this
Twenty-seventh Day of December, 2022

*Katherine Kelly Vidal*
Katherine Kelly Vidal
*Director of the United States Patent and Trademark Office*

Column 17, Line 3, should read as follows:
2. A compound comprising:

or a pharmaceutically acceptable acid addition salt thereof,
wherein:
X is an anticancer compound comprising a nucleoside antimetabolite having the structure:

wherein:
B is natural or modified nucleic acid base,
$R^2$ and $R^3$ are independently selected from the group consisting of H, OH, F, and Cl; and
Y is selected from the group consisting of H, alkyl, aryl, substituted aryl, heteroaryl, and substituted heteroaryl.